United States Patent [19]

Vinci

[11] Patent Number: 5,549,121
[45] Date of Patent: Aug. 27, 1996

[54] SURGICAL ARM SUPPORT

[76] Inventor: Vincent A. Vinci, 20 Willard St., Lodi, N.J. 07644

[21] Appl. No.: 507,059

[22] Filed: Jul. 25, 1995

[51] Int. Cl.$^6$ .................................................. A61F 5/37
[52] U.S. Cl. ................... 128/878; 128/879; 128/DIG. 15
[58] Field of Search ..................... 128/849–856, 128/877–879, 888, DIG. 15, 845, 846, 882; 602/41, 60, 61, 65, 4, 20–23

[56] References Cited

U.S. PATENT DOCUMENTS

| | | |
|---|---|---|
| 794,457 | 7/1905 | Gaiter . |
| 1,219,453 | 3/1917 | Hansen . |
| 2,084,305 | 6/1937 | Bach . |
| 2,245,293 | 6/1941 | Ogburn . |
| 3,817,245 | 6/1974 | Kroeger ........................... 128/DIG. 15 |
| 3,884,225 | 5/1975 | Witter ..................................... 128/869 |
| 3,889,668 | 6/1975 | Ochs ....................................... 128/870 |
| 4,662,366 | 5/1987 | Tari . |
| 4,858,625 | 8/1989 | Cramer .................................. 128/876 |
| 4,911,179 | 3/1990 | Brown et al. . |

*Primary Examiner*—Michael A. Brown
*Attorney, Agent, or Firm*—Klauber & Jackson

[57] ABSTRACT

An arm support for supporting a patient's arm(s) during surgical and medical procedures such as angioplasty has an elongated rectangular strip of flexible fabric long enough to pass laterally beneath the supine body of such a patient, with lateral strips of mating fastening means such as VELCRO® adjacent each end of the strip's upper surface when in use, and two sets of at least two longitudinal strips of mating fastening means positioned on either side of the upper surface of a central portion where the patient's torso is to be positioned, which mate with the latter strips when each end of the fabric strip is looped about the patient's arm(s) for support.

8 Claims, 5 Drawing Sheets

SURGICAL ARM SUPPORT

BACKGROUND OF THE INVENTION

1. Field of the Invention

The present invention relates to arm supports for use in surgical and medical procedures, and more particularly to a surgical device comprising an arm support for both supporting and locating a patient's arm(s) in order to provide comfort to the patient and to facilitate imaging of the patient by radiographic or other means during angioplasty procedures and the like, where the patient is supported in a supine position on an examining or operating table.

2. Brief Description of the Prior Art

In certain invasive surgical and medical procedures, a patient is located in supine position on a table or the like with one of a variety of imaging or radiographic techniques being used to provide an instantaneous or continuing representation of the patient's condition or response to the procedure. These procedures are often very time consuming and tiring to the patient. Often such procedures are directed toward the patient's coronary system and require accurate imaging of the chest cavity, particularly around the heart.

Furthermore, in order to obtain an accurate or more complete representation of the patient's condition, it is necessary to carry out the imaging techniques along a variety of axes in order to provide a more accurate or complete representation of a three-dimensional nature.

In particular, the present invention contemplates surgical and medical procedures having the object of reducing or eliminating blockage in the coronary system, especially adjacent the heart. The earliest of these procedures, and that used most commonly in the past, was the coronary bypass involving the use of surgical techniques for treating or removing the cause of blockage.

More recently, surgical techniques which are less extensive and invasive in nature have been developed for this purpose and are commonly used instead of coronary bypass surgery where possible. One such technique involves angioplasty procedures wherein a balloon catheter is introduced into the coronary arteries. This procedure is particularly effective for treating coronary blockage caused by localized deposits of plaque on the walls of the coronary vessels. The balloon catheter is caused to move through the coronary vessel until it is aligned within the constriction caused by the plaque. The balloon catheter is then expanded to form an enlarged passage through the vessel by causing the plaque to be adhered to the vessel wall.

Numerous variations of such angioplasty techniques are well known to those skilled in the art and do not require further discussion to permit a complete understanding of the present invention. However, it is noted that angioplasty, including newly developed laser angioplasty, may be either brachial or femoral in nature. That is, the catheter is introduced into the coronary system through an incision in the arm in brachial angioplasty or in the leg in femoral angioplasty.

In all such angioplasty techniques as well as in bypass surgery itself, very accurate radiographic imaging is necessary in order to properly observe the lesion or blockage in the coronary system and the effect of the treatment. Such an image or angiogram is obtained as a precursor to bypass surgery for diagnostic purposes. Similarly, angiographic procedures may be employed before, during and after angioplasty procedures to diagnose the initial condition of the patient and to monitor the effect of the procedure on the patient. Normally, the patient is placed in a supine position on an examining or operating table or the like, and imaging is carried out with the use of a C-arm as a source of focused radiological emissions, being adapted to rotate about the patient so that the coronary system can be viewed from all angles.

Because of the relatively massive size of such imaging equipment, the area in which the patient is located within the rotating C-arm is quite limited. Furthermore, provision is normally made for immobilizing the patient's right arm during imaging, both to prevent the arm from interfering with the obtaining of clear images of the coronary system and also to maintain the patient in a fixed position while a number of images are obtained. In the past, the patient's right arm was arranged on rigid arm boards extending laterally from the side of the table supporting the patient.

With the patient in this position, it has been relatively easy in the past to obtain anterior-posterior or vertical views of the coronary system and even slightly angular views with the C-arm rotated to permit imaging along a plane inclined from vertical. However, fully angular or lateral imaging has presented difficulties for a number of reasons. Initially the laterally extending arm boards often physically interfere with the C-arm because of the relatively limited space provided for the patient and supporting table. Furthermore, with the arm boards extending laterally from the table, the patient's right arm tends to be positioned in or near the plane of the patient's heart which, as noted above, is the area of prime interest in such angiographic techniques.

Thus, both the patient's arm and the arm board tend to detract from fully angular or lateral images since they are at least somewhat radiopaque and tend to cast shadows in the angiograms.

This difficulty in obtaining angular angiograms naturally tends to interfere with the proper diagnosis and treatment of the patient by angioplasty techniques as well as with bypass surgery and the like where accurate and many angled images are required.

Accordingly, there has been found a need for improved apparatus for facilitating angular imaging of the coronary system of supine patients arranged on a supporting table or the like. In perfecting the present invention, it was initially discovered that prior restraints such as arm boards used in these procedures were undesirable for at least two reasons. Initially, the arm boards extended laterally from the table supporting the patient so that the arm boards as well as the patient's arm located on the arm boards tended to physically interfere with necessary rotation or positioning of the imaging equipment. Furthermore, both the patient's arms and the arm boards often prevented the obtaining of precise angular images because of their relatively radiopaque nature and the position of the patient's arm generally in the plane of the heart.

Tari's U.S. Pat. No. 4,662,366 discloses an immobilizing arm support which purports to solve some of these problems. The support includes a flexible sheet adapted for being wrapped about the patient's upper and lower arm and held in place by straps, an immobilizing strap being attached to this sheet for engagement with the table supporting the patient and an extension of the sheet being wrapped about the patient's wrist or hand for supporting and preventing rotation of the lower arm. The sheet can include a pocket for holding a rigidifying panel to minimize flexure of the patient's arm, and the immobilizing strap can be a separate element for attachment and detachment with the sheet.

However, this system, as illustrated in FIG. 1 of the patent, is complicated to install and remove and may cause delays in providing emergency medical treatment when necessary in the course of angioplasty or similar procedures.

U.S. Pat. Nos. 1,219,453; 2,245,293 and 4,911,179 disclose various types of patient restraints for use in non-surgical contexts in which a patient lies atop the central portion of a restraint device and limb-encircling portions on either side secure his limbs.

U.S. Pat. Nos. 2,084,305 and 794,457 disclose patient restraining devices including straps which cross over a patient's torso and include straps for encircling a patient's arms.

Since patients undergoing angioplasty and similar procedures may at any time require movement for emergency medical treatment, it is clear that there is a need for a simple but effective surgical arm support which can be installed and removed quickly and easily.

SUMMARY OF THE INVENTION

It is therefore an object of the present invention to provide a surgical arm support for supporting a patient's arm(s) and facilitating angular radiographic imaging during angioplasty procedures and the like, with the patient being supine on a supporting table or the like, while avoiding or overcoming at least some of the problems discussed above. It is a further object of the invention to provide a surgical arm support in a one-piece form which can be quickly and easily installed or removed.

In accordance with the present invention, an improved surgical arm support comprises an elongated rectangular strip of flexible fabric long enough to pass laterally beneath the supine body of a surgical patient, having lateral strips of mating fastening means adjacent each end on the upper surface when said support is in use and two sets of at least two longitudinal strips of mating fastening means positioned on either side of the upper surface of a central portion of the fabric strip where the patient's torso is to be positioned, so as to mate with the latter strips of mating fastening means when each end of the fabric strip is looped about the patient's arms to support them. The fabric strip is wide enough to support the arm(s) without obstructing access to the arm for intravenous devices, catheters or the like.

Further in accordance with the present invention, a process is provided for supporting at least one arm of a supine surgical patient by arranging a surgical arm support as described above with a central portion under the patient's back, looping at least one end thereof around the arm(s) and securing the lateral strip(s) of fastening means to the longitudinal strips of fastening means so as to immobilize at least one of the arms.

These and other objects and advantages of the invention will be apparent from perusal of the following detailed description, including the appended claims and drawing.

DETAILED DESCRIPTION OF THE INVENTION

Figure 1:
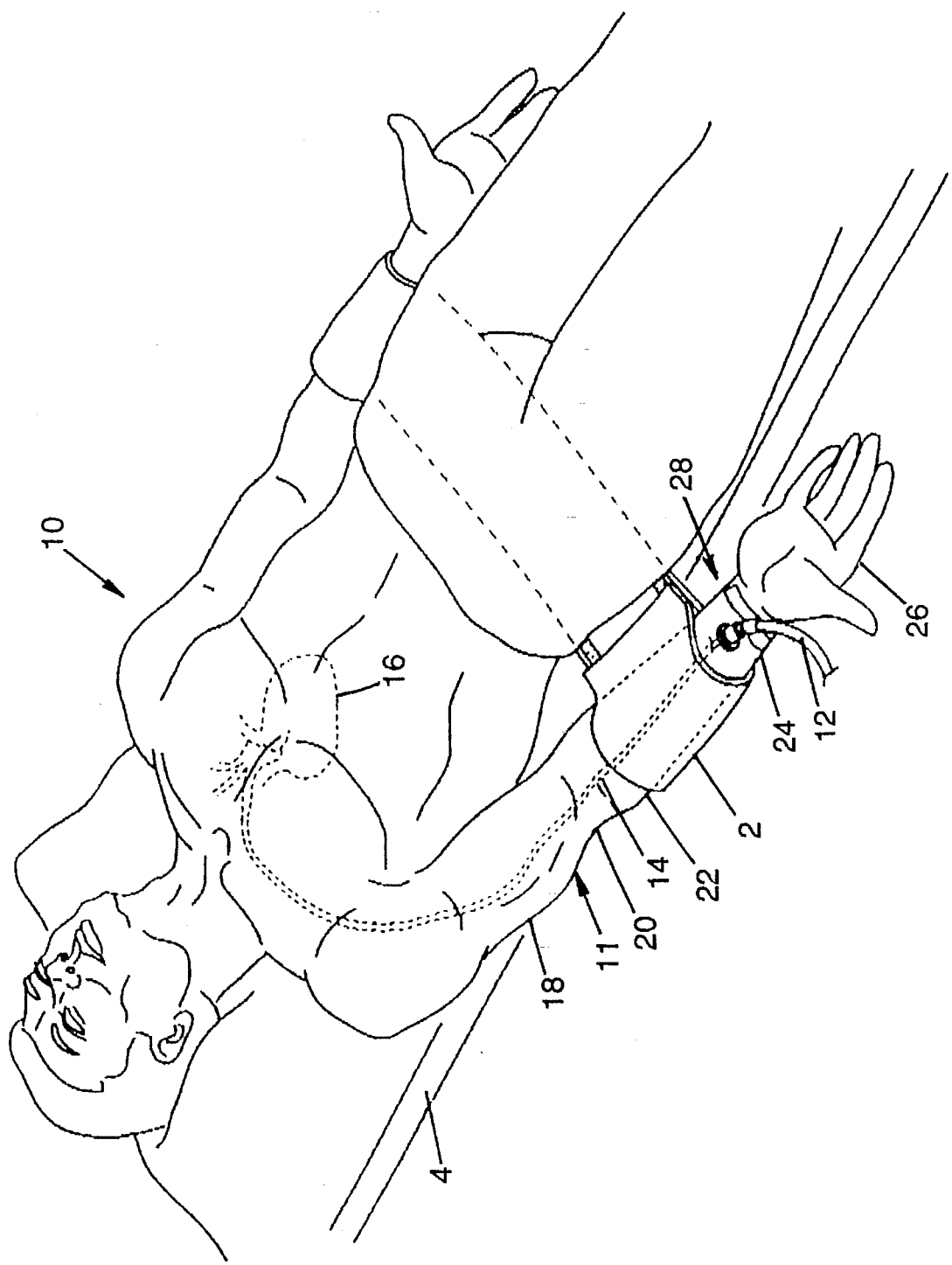
FIG. 1 is a perspective view of a patient catheterized through the arm, located supine on a table with a surgical arm support of the invention passing under the patient's body and positioning both arms.
Figure 2:
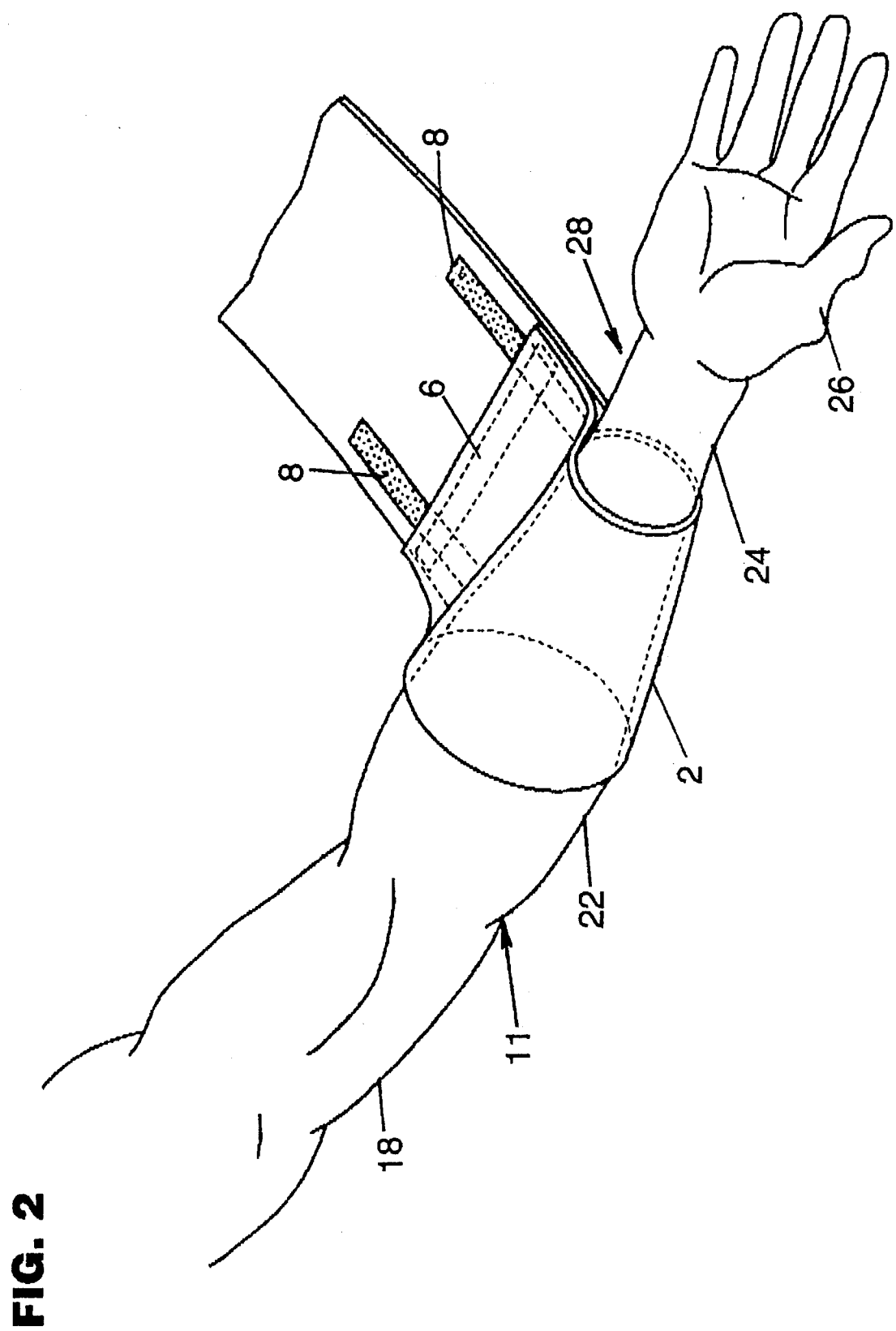
FIG. 2 is an enlarged view of the surgical arm support of the invention as shown in FIG. 1, including only the patient's right arm.
Figure 7:
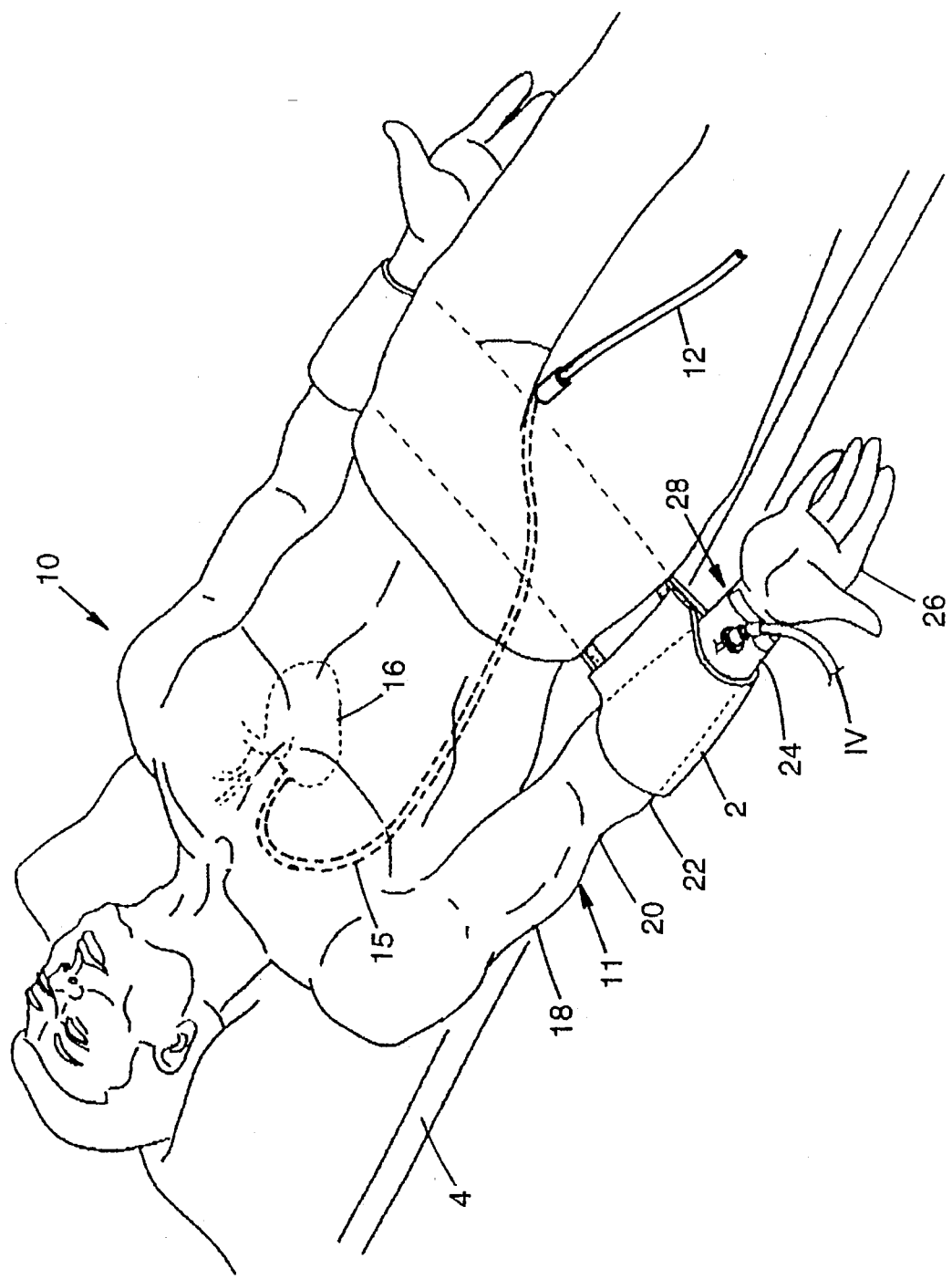
FIG. 7 is a perspective view of a patient catheterized through the leg, located supine on a table with a surgical arm support of the invention passing under the patient's body and positioning both arms.

Referring now to the drawings in combination, a surgical arm support 2 is shown both independently and in use with a patient. The arm support comprises an elongated rectangular strip of flexible fabric suitable for passing under the patient's back and wrapping about the patient's arm(s) as illustrated in FIGS. 1, 2 and 7. Preferably, the width of the strip 2 is selected to leave a portion of the patient's lower or forearm exposed below the strip as illustrated in FIGS. 1 and 2 to facilitate the insertion of catheters 12 and the like into, e.g., the brachial artery in the arm 14 and the femoral artery 15 in the leg.

With the patient 10 being positioned supine on a supporting table 4 or the like, the arm support 2 is intended to support at least the patient's entire right arm 11 including the upper arm 18, elbow 20, lower or forearm 22, wrist 24 and the hand 26 as discussed below. The portion of the forearm 22 left exposed by the arm support 2 is indicated at 28.

Figure 3:
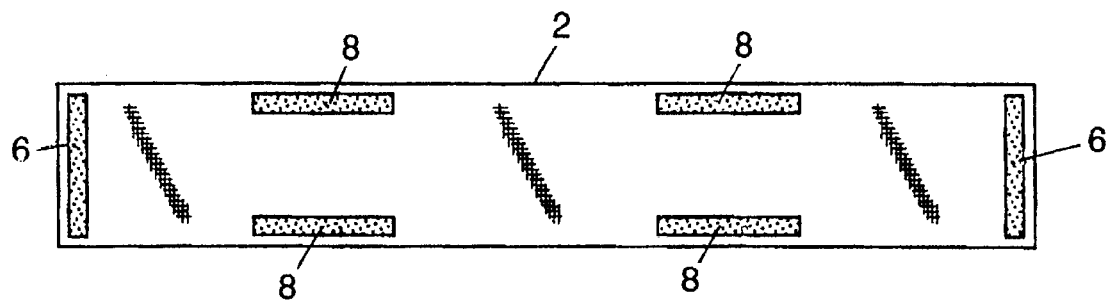
FIG. 3 is a detailed top view of the arm support of the invention.

As shown in FIG. 3, the arm support of the invention is constructed in a manner which is ingeniously simple but effective for its intended purpose. The strip has an elongated rectangular shape, being long enough to pass under a patient's torso with the two ends looped about the patient's arms, say about four feet long, and wide enough to support the arm(s) without covering too much of the forearm, generally less than about eight inches in width and preferably about six inches or more in width. These sizes can be adjusted to meet the needs of very large or very small patients.

Figure 4:
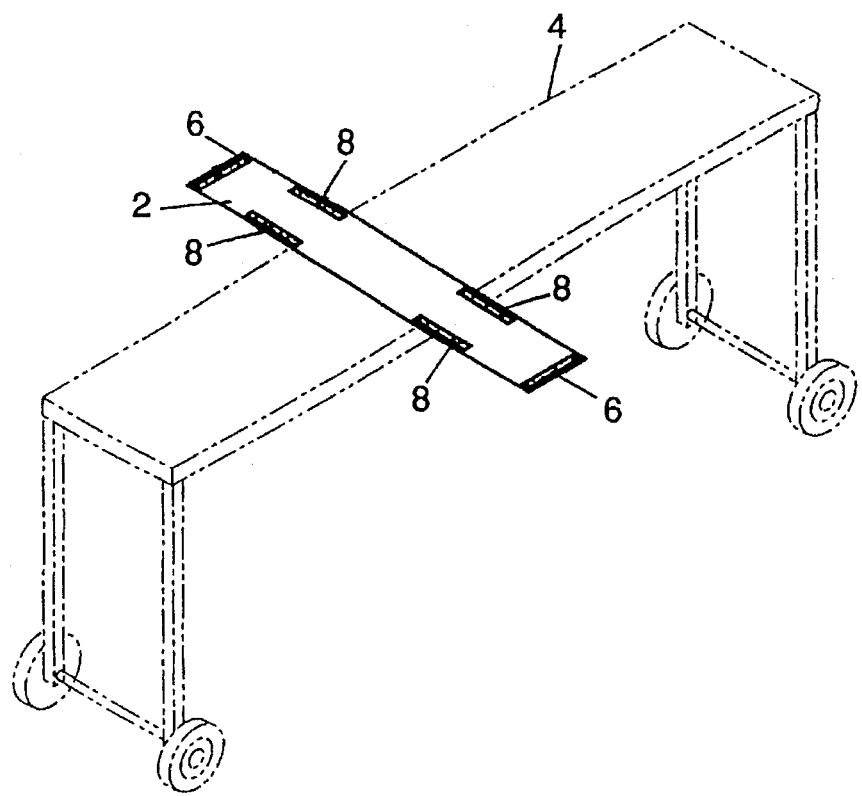
FIG. 4 is a perspective view of the arm support of the invention laid out across an operating table.
Figure 5:
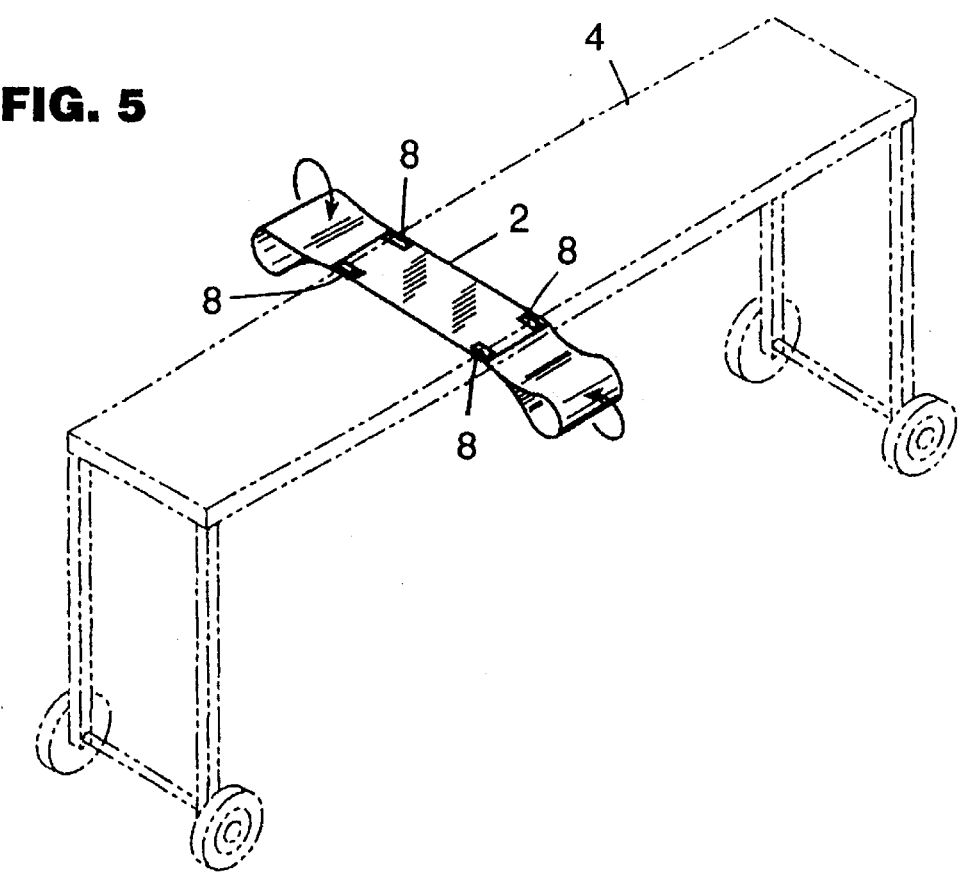
FIG. 5 is a perspective view of the arm support and table of FIG. 4, with the ends of the arm support curled over to accommodate a patient's right and left arms.
Figure 6:
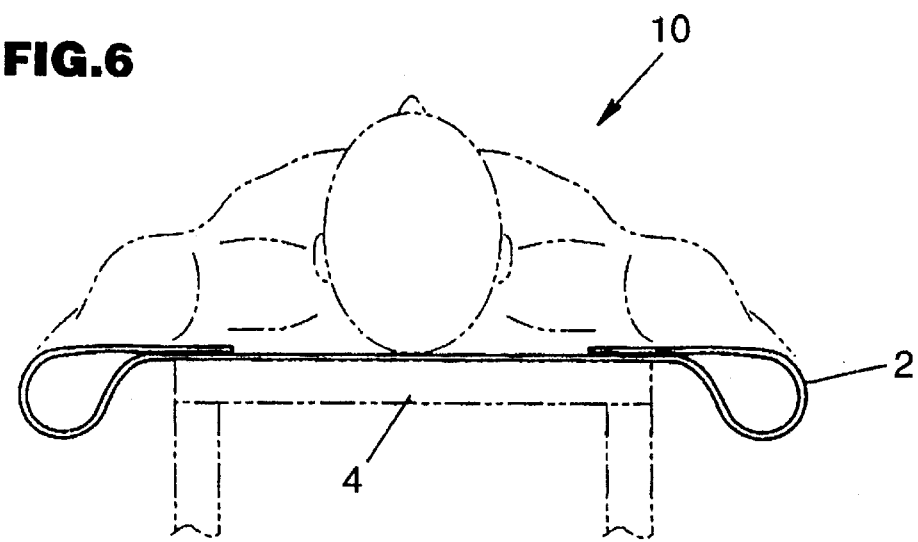
FIG. 6 is an end view of a patient supine on the operating table of FIGS. 4 and 5, showing both arms supported by the arm support of the invention.

At each end of the upper surface of the strip (in position for intended use), as shown in FIG. 4 lateral strips 6 of mating fastening means are provided. Adjacent the central portion of the fabric strip, longitudinal strips 8 of such mating fastening means are provided, positioned so as to mate with the material of strips 6 when the ends of the fabric strip are looped about the arm(s) of the patient to support same. As shown in FIGS. 5 and 6 these mating fastening means are preferably hook and loop fabric portions, respectively, so that strips 6 and 8 will mate with each other. Such hook and loop fabric is available commercially, e.g., as VELCRO® from the Velcro Corporation. Other commercial suppliers of similar hook and loop fabric fastening means exist which can provide the necessary materials from which to fashion the arm support of the present invention. However, it is necessary to observe the importance of the relative gripping strength of these fastening materials. Since the arm of a human patient is being supported in a sometimes critical procedure, it is essential that the fastening device not come unfastened unintentionally. Accordingly, only those hook and loop fabric fastening means which require significant energy to disengage them should be employed. Also, to minimize possible discomfort to the patient, lateral strips 6 are preferably the hook fabric material, while longitudinal strips 8 are the loop fabric material.

As illustrated in FIGS. 1 and 2, it can be seen that the patient's upper arm 18 is inclined generally downward so that a substantial portion of the upper arm and preferably the entire forearm are positioned substantially below the plane of the patient's heart 16 to facilitate angular imaging. Thus, through this simple but effective device, the patient's arm is supported in a position closely adjacent to the table 4 and below the plane of the patient's heart to facilitate radiographic imaging of the coronary system and other portions of the patient's chest cavity as well. The position of the patient's arms also facilitates positioning and movement of imaging equipment, particularly a C-arm which is commonly adapted for rotation relatively close to the table 4.

The fabric strip forming the arm support of the present invention can be formed from any suitable fabric, made from natural or synthetic fibers.

Cotton muslin is one preferred fabric. The material from which the arm support of the present invention is fashioned is preferably of a flexible nature, i.e., it is pliable and not stiff or resistant to folding and wrapping. It should not be, however, made from one of the stretch fabrics that are commonly used in medical appliances, since the surgical device of the present invention has as its primary function the support of the arm. It is not a restraining device, which would be a tendency of a stretch fabric. The stretch fabric would also tend to cut off circulation to the arm that it was supporting. Preferably the fabric is made from radiolucent materials such as polypropylene, and materials which are inexpensive, e.g., a nonwoven material composed of high density polyethylene fibers such as Tyvec®, in order to obtain an arm support surgical device which is disposable. This would appear to be the most likely mode of use in view of current procedures. However, if an arm support device were desired which is reusable, then attention would have to be paid to the ability of the material chosen to withstand sterilization procedures, e.g., autoclaving. Tyvec® would be a suitable material for this mode of use as well.

EXAMPLES

The invention will be further illustrated by working examples. The arm support of the invention was employed to support the arms of several patients during several procedures of cardiac catheterization and angioplasty. These are time-consuming and prolonged procedures in which the patient is coherent and is required to respond to doctor-patient questions during the process. Without such support, the patient's arms become tired, and an operating room technician or nurse must assist with adjustments for the patient's comfort. Such problems are exacerbated when the patient is broad of build or overweight, as the operating table is necessarily relatively narrow in order to accommodate various radiographic equipment and the like closely adjacent to the patient. Prior art supports such as that disclosed in U.S. Pat. No. 4,662,366 were considered inappropriate, since they would require excessive time for removal in medical emergencies. Surprisingly, it was found that the surgical arm support of the invention supported either or both arms in stable positions, permitting the physician to proceed directly with the procedures without interruption for patient complaints or adjustments. Additional convenience was gained in that the arm support can be loosened and used for an additional body-lift strap when moving the patient on and off the operating table. Because the support was simple and quickly installed and removed, the physicians felt comfortable employing it during the delicate procedures of catheterization and angioplasty. Many variations in the use of the surgical arm support as disclosed are possible, as will be apparent from the preceding description. Accordingly, the scope of the present invention is limited only by the following appended claims.

What is claimed is:

1. An arm support for use in surgical and medical procedures performed on a patient comprising an elongated rectangular strip of flexible fabric long enough to pass laterally beneath the supine body of said patient, having lateral strips of mating fastening means adjacent each end on the upper surface when said support is in use, and two sets of at least two longitudinal strips of mating fastening means positioned on either side of the upper surface of a central portion of said strip where said patient's torso is positioned, so as to mate with said lateral strips when each end of said strip is looped about the patient's arms to support them.

2. The surgical arm support of claim 1 wherein said mating fastening means comprise hook and loop fabric portions.

3. The surgical arm support of claim 1 which is about 4 feet long and from about 6 to about 8 inches wide.

4. The surgical arm support of claim 1 wherein said fabric is woven.

5. The surgical arm support of claim 4 wherein said fabric is cotton muslin.

6. The surgical arm support of claim 1 wherein said fabric is nonwoven.

7. The surgical arm support of claim 6 wherein said fabric is a material composed of high density polyethylene fibers.

8. A method for supporting at least one arm of a patient who is the subject of a surgical or medical procedure and is supported in a supine position on an examining or operating table, comprising:

arranging laterally beneath said patient's back the central portion of an arm support comprising:
an elongated rectangular strip of flexible fabric long enough to pass laterally beneath the supine body of said patient, having lateral strips of mating fastening means adjacent each end on the upper surface when said support is in use, and two sets of at least two longitudinal strips of mating fastening means positioned on either side of the upper surface of a central portion of said strip where said patient's torso is positioned, so as to mate with said lateral strips when each end of said strip is looped about said patient's arms to support them;
looping at least one end thereof around said arm(s) and securing the lateral strip(s) of said fastening means to said longitudinal strips of fastening means so as to support said arm(s).

\* \* \* \* \*